(12) United States Patent
Somekh et al.

(10) Patent No.: US 6,381,021 B1
(45) Date of Patent: Apr. 30, 2002

(54) METHOD AND APPARATUS FOR MEASURING REFLECTIVITY OF DEPOSITED FILMS

(75) Inventors: Sasson Somekh, Los Altos Hills; Manoocher Birang, Los Gatos, both of CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/602,569

(22) Filed: Jun. 22, 2000

(51) Int. Cl.[7] .............................................. G01N 21/55
(52) U.S. Cl. ..................................................... 356/445
(58) Field of Search ................................ 356/445, 446, 356/72, 73, 381, 382; 117/93, 102, 201; 250/559.27

(56) References Cited

U.S. PATENT DOCUMENTS

| | | | |
|---|---|---|---|
| 4,496,425 A | * 1/1985 | Kuyel | 156/626 |
| 4,819,167 A | 4/1989 | Cheng et al. | 364/167.01 |
| 4,955,979 A | 9/1990 | Denayrolles et al. | 374/131 |
| 4,956,538 A | 9/1990 | Moslehi | 219/121.6 |
| 4,969,748 A | 11/1990 | Crowley et al. | 374/1 |
| 4,984,902 A | 1/1991 | Crowley et al. | 374/1 |
| 5,143,552 A | 9/1992 | Moriyama | 118/666 |
| 5,303,671 A | 4/1994 | Kondo et al. | 118/719 |
| 5,362,969 A | 11/1994 | Glenn | 250/561 |
| 5,483,138 A | 1/1996 | Shmookler et al. | 318/568.16 |
| 5,536,359 A | 7/1996 | Kawada et al. | 156/626.1 |
| 5,563,798 A | 10/1996 | Berken et al. | 364/478.06 |
| 5,568,978 A | * 10/1996 | Johnson et al. | 374/161 |
| 5,738,440 A | 4/1998 | O'Neill et al. | 374/9 |
| 5,969,805 A | * 10/1999 | Johnson et al. | 356/72 |
| 6,001,175 A | * 12/1999 | Maruyama et al. | 117/102 |

\* cited by examiner

*Primary Examiner*—Frank G. Font
*Assistant Examiner*—Michael P. Stafina
(74) *Attorney, Agent, or Firm*—Moser, Patterson & Sheridan LLP (57) ABSTRACT

The present invention provides a method and apparatus for measuring the reflectivity of a substrate surface in situ. A transmitting assembly includes a light source positioned externally to a vacuum chamber and proximate an opening to transmit an optical beam into the vacuum chamber. An optical beam supplied by the light source is transmitted into the chamber via one or more optical devices such as fiber optics cables, lens and the like. Reflected portions of the optical beam are collected by a receiving assembly. A signal processing system coupled to the receiving assembly is programmed to determine the reflectivity of a substrate disposed in the vacuum chamber.

27 Claims, 8 Drawing Sheets

METHOD AND APPARATUS FOR MEASURING REFLECTIVITY OF DEPOSITED FILMS

BACKGROUND OF THE INVENTION

1. Field of the Invention

The present invention relates to a semiconductor processing. More particularly, the invention relates to reflectivity measurement and deposited films in situ or online.

2. Background of the Related Art

In the fabrication of integrated circuits and other electronic devices, multiple layers are deposited and etched from substrates in order to form features on the substrate. One important aspect of forming electronic features is photolithography. Photolithography is the patterning of the layers formed on the substrate for removal using an etching process. In a photolithography process, a material such as a photoresist is deposited on the top surface of the layers formed on the substrate and is then patterned by exposing portions of the photoresist to a light source. The exposed portions of the photoresist are determined by a mask which is patterned to define the features which are desired on the substrate. Depending on whether the photoresist is a positive or negative photoresist, either the exposed portion of photoresist or the unexposed portion of photoresist is removed by reacting the photoresist with one or more chemicals. The etching process then selectively etches the under-layers exposed through the remaining photoresist material.

As features sizes decrease, patterning lines and other features on substrates has become increasingly important and difficult. In particular, the effect of the under-layers in scattering the light used to cure the photoresist should be avoided. Otherwise, the patterning of the photoresist will be less than desired. As a result, anti-reflective coatings (ARC) such as dielectric anti-reflective coatings (DARC) are typically employed to ensure that the light used to expose the photoresist in the photography process is not scattered but rather absorbed.

Deposition techniques are currently known in the art which can deposit conventional dielectric ARC materials. However, over time, processes can vary, resulting in the inability of the dielectric ARC materials to achieve the desired reflectivity. Accordingly, the reflectivity of the dielectric ARC materials is periodically measured during processing. Reflectivity can typically be determined by the thickness as well as the quality of the deposition formed on the substrate.

In order to ensure that the dielectric ARC material is adequate to support the application in which it is used, the wafers are periodically moved to a stand-alone chamber where the reflectivity of the film can be measured using conventional optical techniques. While this conventional methodology is useful to determine whether or not the process is adequate on the particular wafer undergoing inspection, moving substrates to separate chambers for measurement is expensive and time-consuming.

Therefore, there is a need for a method and apparatus for determining the reflectivity of arc materials, anti-reflective coating materials in situ or on-line.

SUMMARY OF THE INVENTION

The invention generally provides an apparatus and method for measuring the reflectivity of an object.

One aspect of the invention provides an apparatus comprising a vacuum chamber comprising an aperture for transfer of the object therethrough and an opening for transmitting an optical signal from a region external to the vacuum chamber into an internal region of the chamber. A transmitting assembly including a light source is positioned external to the vacuum chamber and proximate the opening to transmit an optical beam into the internal region. The apparatus further comprises a receiving assembly adapted to receive a reflected portion of the optical beam and a signal processing system coupled to the receiving assembly. The signal processing system is programmed to determine the reflectivity of a surface of a substrate disposed in the vacuum chamber.

Another aspect of the invention provides an apparatus comprising a vacuum chamber body defining an aperture for transfer of the object therethrough, a showerhead disposed on the vacuum chamber body, a substrate support member disposed in the vacuum chamber body, a transmitting assembly and a receiving assembly. The transmitting assembly comprises a light source positioned in a region external to the vacuum chamber body and one or more transmitting cables having a light input end disposed proximate the light source and a light output end adapted to deliver an optical beam into an internal region of the vacuum chamber body. At least a portion of the transmitting cable is disposed in the showerhead. At least a portion of the receiving assembly is disposed in the internal region and is adapted to receive a reflected portion of the optical beam.

Another aspect of the invention provides a method for measuring reflectivity of a substrate disposed in a vacuum processing chamber comprising a gas showerhead at one end of the chamber. The method comprises delivering an optical beam through the showerhead and onto a surface of the substrate and receiving reflected portions of the optical beam at a signal receiving assembly. In one embodiment, the step of delivering comprises emitting the optical beam onto a surface of the showerhead, wherein the optical beam is reflected from the surface of the showerhead onto the surface of the substrate.

Another aspect of the invention provides a method for measuring reflectivity of a substrate disposed in a vacuum processing chamber gas having a showerhead at one end of the chamber. The method comprises delivering an optical beam from a region lateral of the substrate and onto a surface of the showerhead, wherein the optical beam is reflected from the surface of the showerhead onto the surface of the substrate. Reflected portions of the optical beam are received at a signal receiving assembly.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present invention provides a method and apparatus for measuring the reflectivity of a substrate surface in situ. A transmitting assembly includes a light source positioned externally to a vacuum chamber and proximate an opening to transmit an optical beam into the vacuum chamber. An optical beam supplied by the light source is transmitted into the chamber via one or more optical devices such as fiber optics cables, lens and the like. Reflected portions of the optical beam are collected by a receiving assembly. A signal processing system coupled to the receiving assembly is programmed to determine the reflectivity of a substrate disposed in the vacuum chamber.

Figure 1:
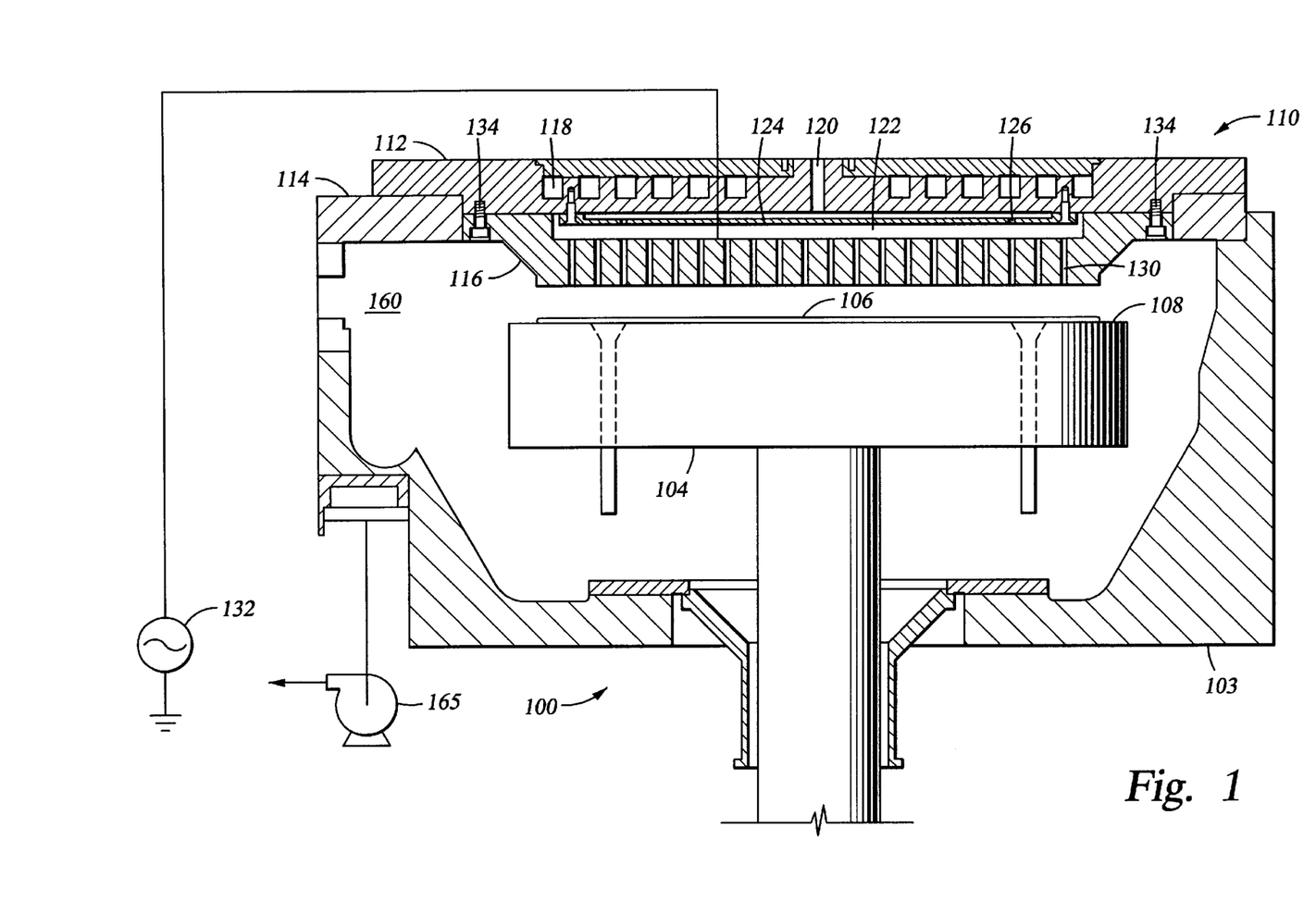
FIG. 1 is side cross sectional view of a CVD processing chamber.

FIG. 1 is side cross sectional view of a CVD processing chamber 100 having a chamber body 103 that defines a cavity. A pedestal 104 is disposed in the cavity of the chamber body 103 and supports a substrate 106 on its upper surface 108 for processing. The pedestal 104 is vertically movable in the chamber 100 to allow the pedestal to be lowered into a substrate loading/unloading position and raised into a processing position. Actuation of the pedestal 104 is achieved by one or more actuators (not shown) coupled to a lower end of the pedestal 104.

The processing chamber 100 includes a lid assembly 110 disposed at an upper end of the chamber body 103. The lid assembly 110 generally comprises a lid rim 114, a backing plate 112 and a showerhead 116 mounted to the backing plate 112. The lid rim 114 is disposed on the chamber body 103 and provides an annular support surface on which the backing plate 112 is disposed. Additionally, the lid rim 114 is an insulating material, thereby insulating the backing plate 112 and the showerhead 116 from the chamber body 103.

The backing plate 112 (also known as a gas-feed cover plate or waterbox) is preferably made of aluminum or an aluminum alloy and operates to control the temperature of the lid assembly 110 during operation. Thus, a fluid channel 118 is formed in the backing plate 112. The fluid channel 118 facilitates the heating or cooling of the backing plate 118 by flowing deionized water or other fluids therethrough.

The backing plate 112 further includes a centrally located process gas inlet 120 adapted to deliver process gas to the showerhead 116. Although not shown, the process gas inlet 120 is coupled to one or more upstream gas sources and/or other gas delivery components, such as gas mixers. The process gas inlet 120 is in fluid communication with a gap 122 defined between the backing plate 112 and the showerhead 116. The gap 122 is shaped and sized to accommodate a blocker plate 124 mounted to the backing plate 112. The blocker plate 124 is preferably made of an aluminum alloy and includes passageways 126 formed therein adapted to disperse the gases flowing from the gas inlet 120 to the showerhead 116.

The showerhead 116 is substantially disc-shaped and is coupled to the lower face of the backing plate 112 by bolts 134 or similar fasteners to ensure good thermal contact. A plurality of holes 130 vertically formed in the showerhead accommodate the passage of gases from the gap 122 to the chamber cavity. A power source 132 is coupled to the showerhead 116 and energizes the showerhead 116 during operation to provide an electromagnetic field in the chamber 100.

A gas supply unit (not shown) provides precursor gases to the chamber 100 which react with the substrate 106 during operation. A vacuum system 165 communicates with a pumping channel 160 formed in the chamber 100 to evacuate the gases from the chamber 100. The vacuum pump 165 and the pumping channel 160 can be selectively isolated by a valve disposed between the pumping channel 160 and the vacuum pump 165.

Multiple embodiments of a monitoring system are provided to generate and detect a signal propagated through the processing region of the chamber 100. The detected signal is processed to provide real-time reflectivity values for the substrate being processed in the chamber 100.

Figure 2:
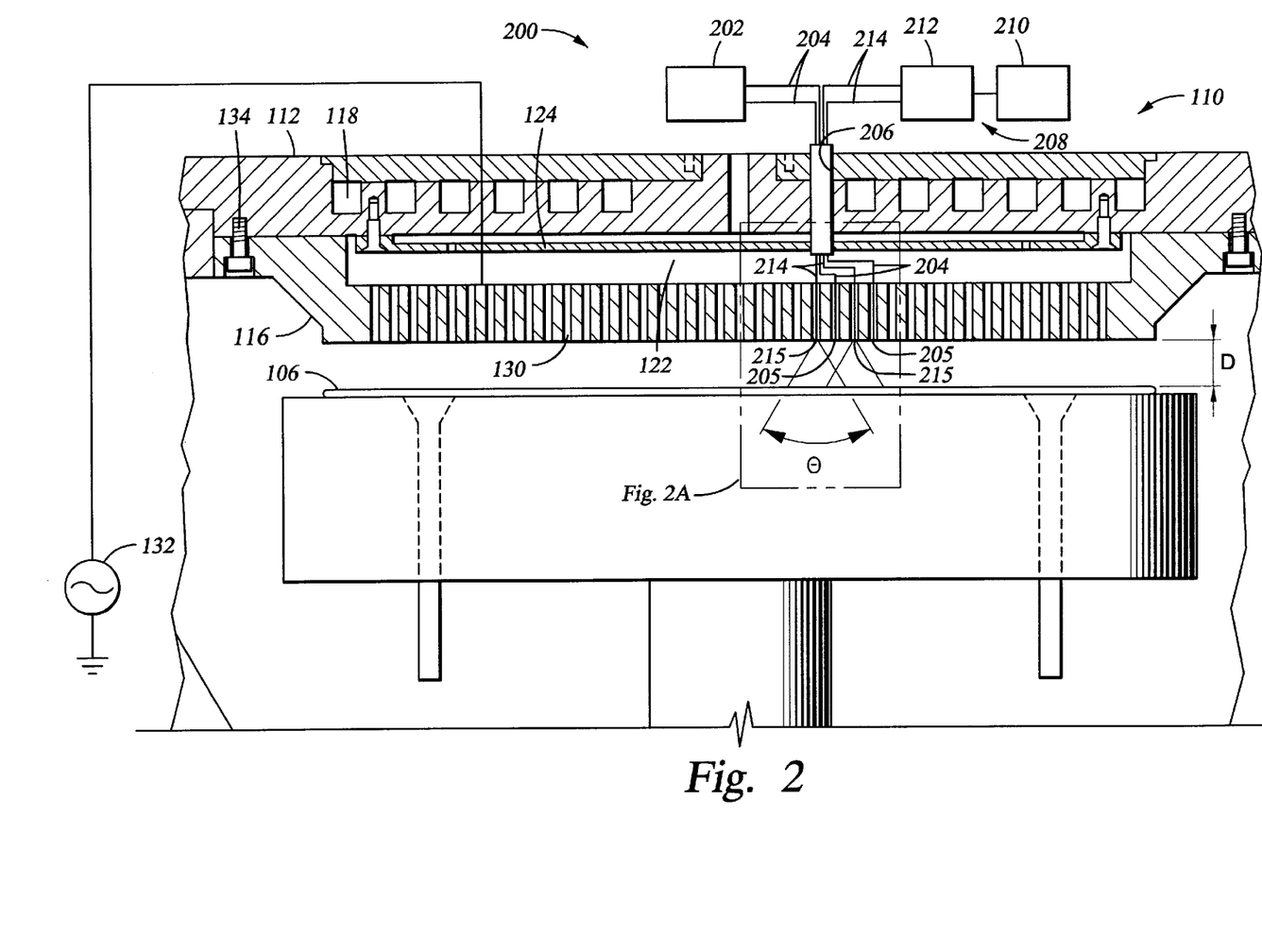
FIG. 2 is a monitoring system for measuring film reflectivity and generally includes a transmitting assembly, a receiving assembly and a signal processing unit.

One embodiment of a monitoring system for measuring film reflectivity is shown in FIG. 2 and generally includes a transmitting assembly 200, a receiving assembly 208 and a signal processing unit 210. The transmitting assembly 200 includes a signal source 202 and output transmission cables 204. The signal source 202 is disposed on or near the chamber 100 to provide a signal of the desired wavelength.

Output transmission cable 204 supports the signal type outputted by the signal source 202 and carries the signal into the chamber 100. Although the embodiment of FIG. 2 shows two output transmission cables 204, any number of cables may be used. The output transmission cable 204 is disposed through an opening 206 formed in the backing plate 112 and extends through the blocker plate 124 and into the showerhead 116. An output end 205 of the output transmission cable 204 is positioned at or near the lower face of the showerhead 116 in facing relation to the substrate 106. The output end 205 may include any number of optical devices adapted to focus or otherwise condition the signal emitted from the output transmission cable 204.

In one embodiment, the receiving assembly 208 includes input cable 214 (two shown) coupled to a detector/converter unit 212. The input cables 214 are preferably fiber optic cables, but any other signal transmission medium may be used. As with the output transmission cables 204, the input transmission cables 214 are disposed through the opening 206 and terminate at a point at or near the lower surface of the showerhead 116. The input ends 215 of the input cables 214 provide collection points for signals propagated from the output transmission cables 204 and may include optical apparatus to facilitate the signal collection.

Figure 2A:
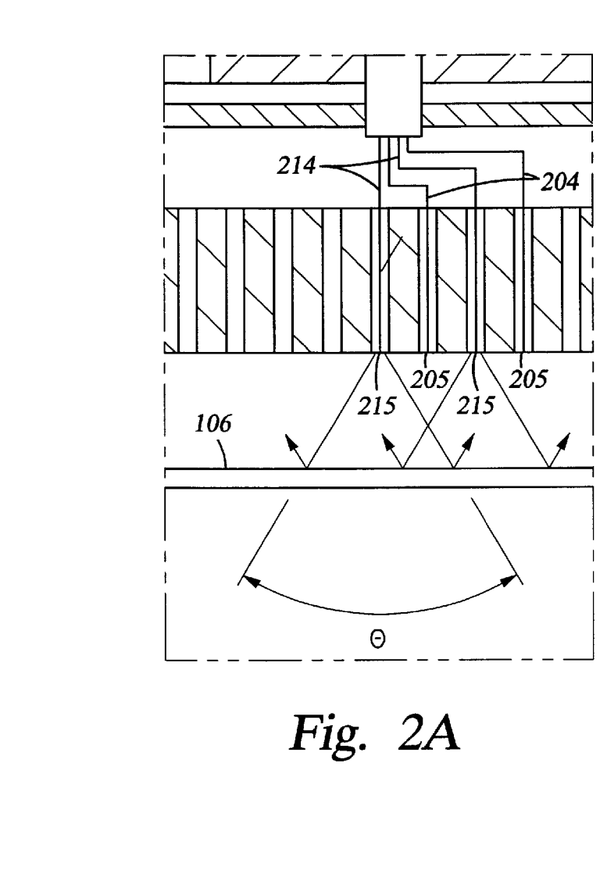
FIG. 2A is a close-up partial view of the monitoring system of FIG. 2.
Figure 3:
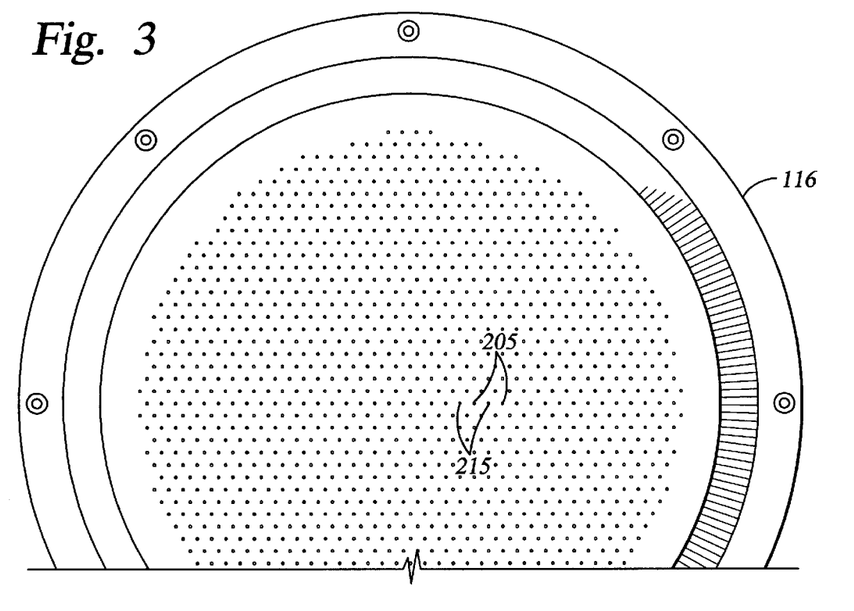
FIG. 3 is a partial bottom view of a showerhead illustrating the positioning of output ends and the input ends of output transmission cables and input transmission cables, respectively.

The relative positioning of the output ends 205 and the input ends 215 is best seen in FIG. 2A and FIG. 3. FIG. 3 shows a bottom view of the showerhead 116 and illustrates the proximity between the output ends 205 and the input ends 215. The close grouping of the output/input ends 205, 215 ensures that the reflected signal strength is within the capture range of the detecting medium (i.e., the input end 215). As illustrated in FIG. 2A, the beam emitted by the output ends 205 is not columnar and diverges according to a beam angle O. Upon striking the substrate 106, the beam is reflected at substantially the same angle O. The reflected beam then propagates with decreasing intensity. In order to receive beam reflections of sufficient strength capable of being detected by the detector/converter unit 212, the input end 205 is positioned near the output end 215. In addition to the lateral proximity to the output end 205, the input end 215 is also close to the reflecting surface of interest, i.e., the upper surface of the substrate 106. The exact position of the output and input ends 205, 215 will depend on a particular application and the specifications of the optical equipment, reflecting surfaces, etc.

Referring again to FIG. 2, the detector/converter unit 212 receives and detects signals from the input cables 214 and produces an output recognizable to the signal processing system 210. Thus, for example, the detector/converter unit 212 may produce an analog signal proportional to the signal received from the input cables 214 and then transmit the analog signal to the signal processing system 210. In one embodiment, the detector/converter unit 212 is a UV-enhanced silicon detector or photo-multiplier.

The signal processing system 210 may be any system adapted to receive signals from the detector/converter unit 212 and produce data pertaining to the reflectivity of the substrate being processed. Although not shown, the signal processing system 210 is preferably connected to, or part of, the control system of the chamber 100 which operates the chamber components during processing. Thus, data provided by the signal processing system 210 can be used to affect the deposition process, such as by terminating the process when a predetermined reflectivity value is measured.

Figure 2B:
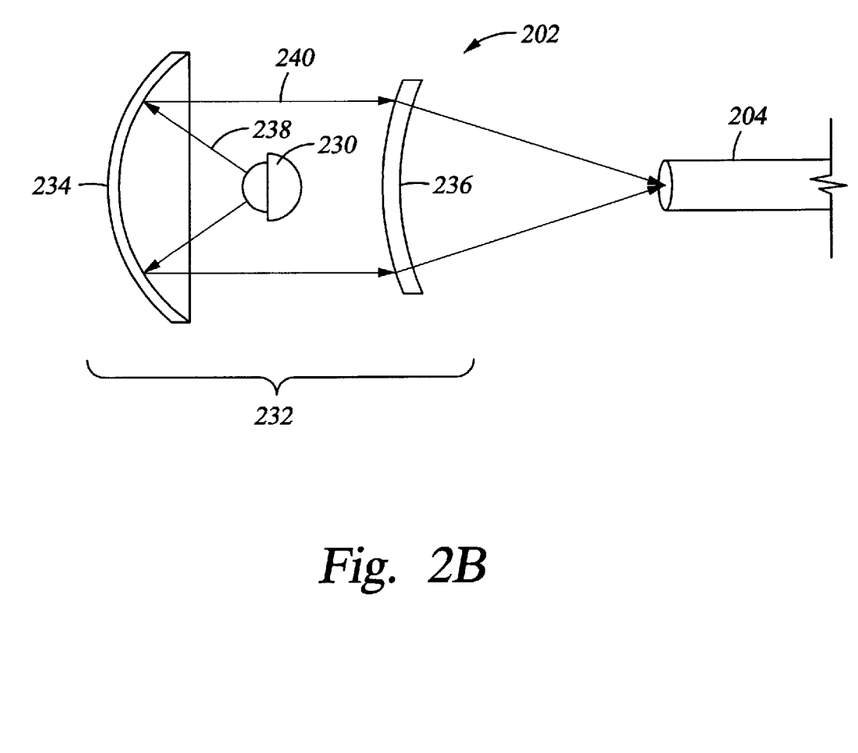
FIG. 2B is a schematic representation of a signal source assembly shown in FIG. 2.

One embodiment of the signal source 202 is shown in FIG. 2B and generally includes a signal generator 230 and an optics assembly 232. The wavelength of the signal generated by the signal generator 230 is selected according to the particular operating parameters of the subsequent lithography process. Specifically, the wavelength of the signal is substantially equal to the wavelength of the light used in the lithography process. In a particular embodiment, the wavelength is 248 nm. In one embodiment, the signal generator 230 is a UV lamp, such as a Mercury Arc Lamp. However, other signal generators are contemplated.

An optical beam 238 produced by the signal generator 230 is controlled and shaped by the optics assembly 232 and then output to the transmission cable 204. Illustratively, the optics assembly 232 may include any combination of lenses, filters, beam splitters, polarizers, etc. A particular embodiment of the optics assembly 232 shown in FIG. 2B includes a parabolic mirror 234 and a convex lens 236. The parabolic mirror 234 is positioned in the path of an optical beam 238 emitted by the signal generator 230. The mirror 234 creates a relatively columnar beam 240 which propagates to the convex lens 236. The numerical aperture of the convex lens 236 is matched to that of the transmission cable 204 so that a substantial portion of the columnar beam 240 is coupled into the transmission cable 204. Although preferably a fiber optics cable, the transmission cable 204 may be any other suitable device (e.g., a crystal rod) adapted to support transmission of a propagating signal.

Figure 4:
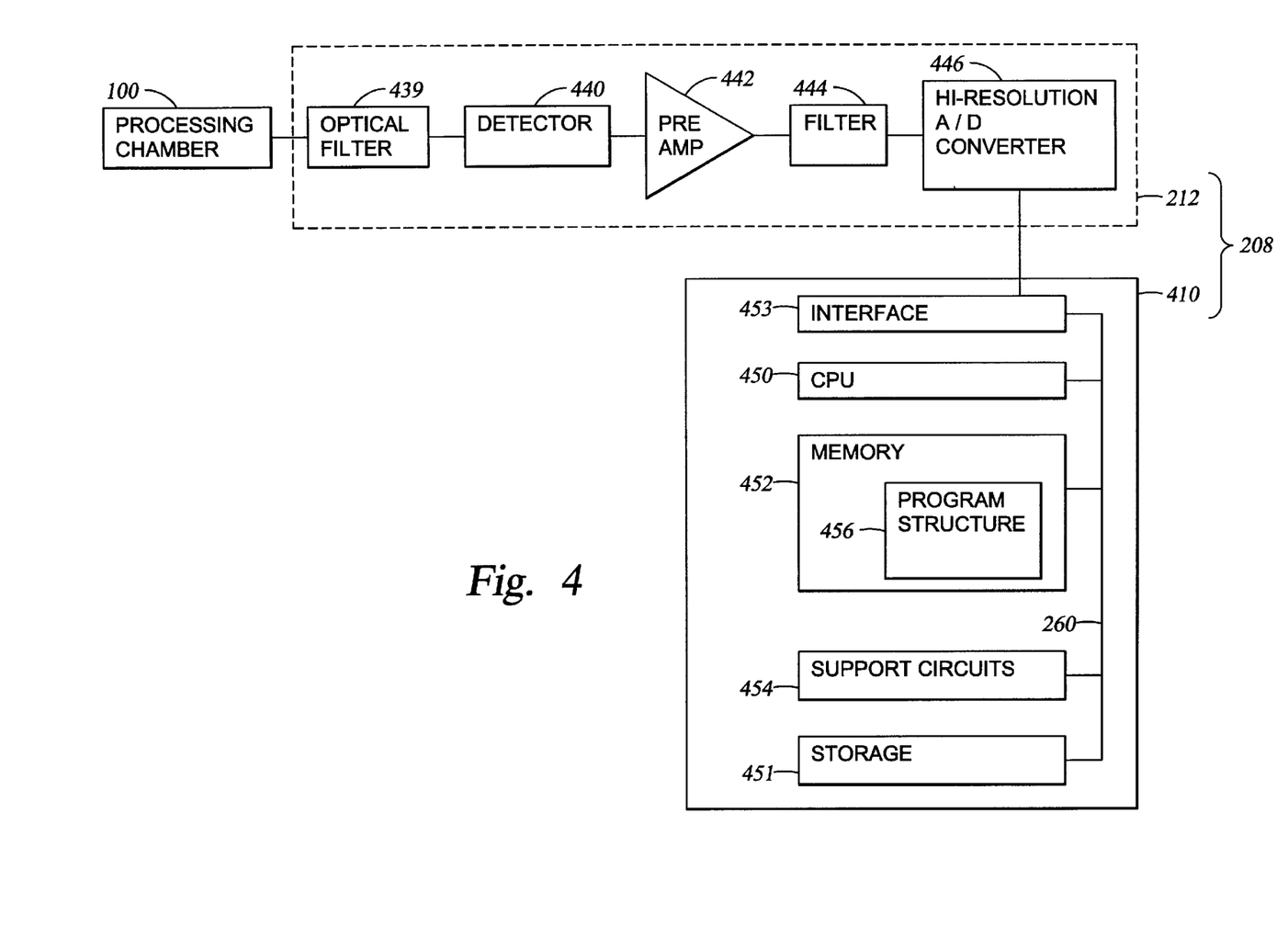
FIG. 4 is a schematic representation of a detector/converter unit and a signal processing system.

A schematic representation of the detector/converter unit 212 and the signal processing system 210 is shown in FIG. 4. The detector/converter unit 212 includes an optical filter 439, a detector 440, a pre-amp 442, a filtering device 444 and an analog-to-digital (A/D) converter 446. The optical filter 439 is adapted to restrict the transmission of an incoming signal (from input cables 214) according to wavelength. In a particular embodiment, the optical filter 439 is selected to block wavelengths greater than 300 nm. The detector 440 is adapted to produce an analog signal proportional to the intensity of the optical signals received from the optical filter 439. The analog signal is then amplified by the pre-amp 442 and filtered by filtering unit 444. The filtering unit 444 may include one or more filters to screen, or block, a portion of the analog signal. For example, the filtering unit 444 may be configured to screen selective wavelengths related to a particular range of frequencies. In one embodiment, the filtering unit 444 acts as a low-pass filter to block high frequency signals. The A/D converter 446 provides a mechanism for converting the analog signal into a signal readable by the signal processing unit 210.

The signal processing system 210 shown in FIG. 4 comprises a bus line 460 coupling a central processing unit (CPU) 450, storage 451, a memory 452, an interface device 453 and support circuits 454 for the CPU 450. The CPU 450 may be any generalpurpose computer processor that can be used in an industrial setting for processing signals received from the detector/converter unit 212. The support circuits 454 are coupled to the CPU 450 for supporting the processor in a conventional manner and may include cache, power supplies, clock circuits, input/output circuitry and subsystems, and the like. The interface device 453 connects the signal processing system 210 to the detector/converter unit 212 as well as other devices which may be connected to a common network. Storage 451 is preferably a Direct Access Storage Device (DASD), although it could be any other storage such as floppy disk drive or optical storage device. Although storage 451 is shown as a single unit, it could be any combination of fixed and/or removable storage devices, such as fixed disk drivers, floppy disk drivers, tape drives, removable memory cards, or optical storage.

Memory 452, or computer-readable medium, is preferably a random access memory (RAM) sufficiently large to hold the necessary programming and data structures of the invention. While memory 452 is shown as a single entity, it should be understood that memory 452 may comprise a plurality of modules, and that the memory 452 may exist at multiple levels, from high speed registers and caches to lower speed but larger DRAM chips. Further, memory 452 and storage 451 could be part of one virtual address space spanning multiple primary and secondary storage devices. As shown in FIG. 4, memory 452 contains a program structure 456. The program structure 456 is a program, or software routine, adapted to perform the various reflectivity analysis described below. When contained by a computer readable medium such as the memory 452 or storage 451, the program structure 456 is referred to as a program product. The contents of memory 452, including the data structure, can be loaded from and stored to the storage 451 as needed by the CPU 450. The program structure 456 may also be stored and/or executed by a second CPU (not shown) that is remotely located from the hardware being controlled by the CPU 450.

In operation, the signal provided by the signal generator 200 is propagated through the optics assembly 201 and output transmission cable 204 and then onto the substrate 106 being processed. Accordingly, a portion of the substrate 106 is illuminated. The spot size of the illuminated area on the substrate is, in part, determined by the beam breath θ and the distance D between the terminal ends of the output transmission cable 204 and the substrate. Either one or both of θ or D may be varied to adjust the spot size on the substrate 106 while the substrate 106 is in a raised processing position. The beam breath θ may generally be controlled by lenses and other optical devices disposed at the output end 205 of the output transmission cables 204. The position of the output end 205 of the transmission cable 204 may be adjusted according to a desired distance between the output end 205 and the substrate 106.

The spot size on the substrate 106 is also adjusted to account for specular reflections caused by devices form on the substrate 106. Specular reflections often occur because the devices on patterned substrates act as micro-mirrors which reflect incident signals in many directions. It is believed that a tight, focused beam will cause scattering and diffraction and serve to exacerbate the problems associated with specular reflections. Accordingly, the spot size is preferably sufficiently large enough to cover multiple dies, thereby minimizing/averaging the effect of the substrate patterns. A relatively large spot size generated using multiple fiber of optics cables acts to integrate the effect of scattering and diffraction caused by the pattern on the substrate 106, thereby improving the signal-to-noise ratio.

The signal output from the out transmission cable 204 is then propagated through the chamber 100 and onto a surface of the substrate 106. Upon striking the substrate 106, the signal is at least partially reflected. A portion of the reflected signal is collected at the input end 215 and transmitted to the detector/converter unit 212 via the input transmission cable 214. In one embodiment, the detector/converter unit 212 generates an analog signal proportional to the intensity of the received optical signal. The resulting analog signal is filtered and then converted into a digital signal readable by the signal processing system 210. The digital signal is processed by the processing unit 210 to determine the reflectivity of the substrate surface.

The signal processing system 210 continuously monitors the reflected signal from the substrate 106 during a process cycle. In one embodiment, the signal processing system 210 receives (e.g., from a human operator) a predetermined reflectivity value correlated to an optimum film quality. The reflectivity value is used as a threshold to compare the detected reflectively signal. The process continues so long as the reflectivity signal is higher than the threshold. Once a determination is made that the reflectivity values is below the threshold value, the signal processing system 210 transmits a termination signal indicating that the endpoint of the process has been reached. The process chamber controller then stops the process upon receiving the termination signal. Accordingly, a real-time reflectivity measurement of the substrate 106 is available and can be used to achieve a desired reflectivity value by terminating the deposition process upon detection of the desired reflectivity value. The endpoint control reduces the variation on the DARC coating reflectivity and provides a consistent film thickness and optical quality.

Figure 5:
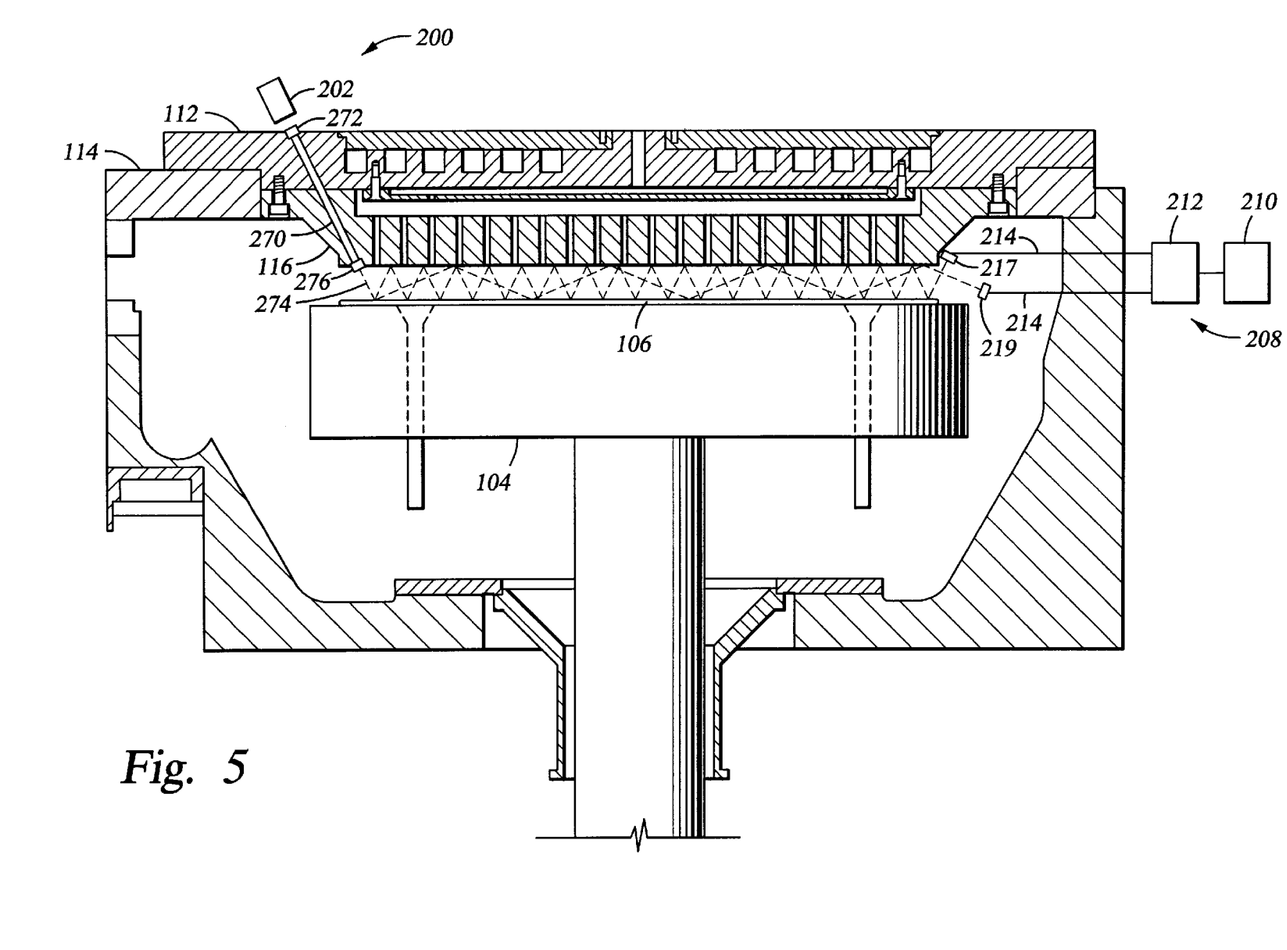
FIG. 5 is another embodiment of a reflectivity monitoring system.

Another embodiment of a reflectivity monitoring system is shown in FIG. 5. An optical channel 270 is formed through the backing plate 112 and the showerhead 116. The optical channel 270 extends from an external opening formed in the backing plate 112 to an internal opening formed in the showerhead 116. Thus, the optical channel 270 provides a pathway into the chamber 100 for an optical signal generated from a location external to the processing region of the chamber 100.

To maintain the integrity of the chamber conditions during processing, a window 272 is disposed at the external end of the optical channel 270. Preferably, the window 272 is a transparent material having a low refractive index in order to prevent excessive refraction of an optical beam. In addition, the window material is selected to allow transmission of a predetermined wavelength or range of wavelengths. Exemplary materials to create the window 272 include quartz, sapphire and fused silica.

Figure 6:
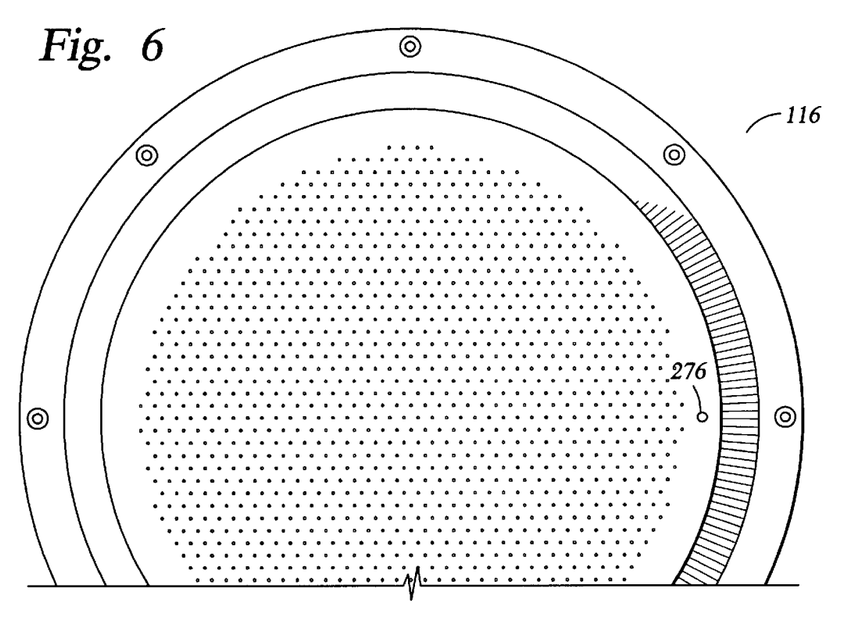
FIG. 6 is a partial bottom view of a showerhead illustrating a positioning of an optical device.

An optical device 276 is positioned at the interior opening of the optical channel 270. The optical device 276 may include one or more lenses or other mechanisms adapted to condition the optical beam 274. For example, the optical device 276 may be a collimator shaped to define a desired spot size on the substrate 106. Referring briefly to FIG. 6, a positioning of the optical device 276 is shown. To minimize interference with the gas outlet holes 130 of showerhead 116, the optical device 276 is located in a perimeter region radially outwardly of the holes 130.

Referring again to FIG. 5, the transmitting assembly 200 is positioned at the external opening of the optical channel 270. Specifically, the signal source 202 and the optics assembly 202 are positioned to emit an optics beam 274 through the window 272, along the optical channel 270 and out through the optical device 276. In one embodiment, the signal source 202 is a coherent light source and the optical channel 270 is machined to a diameter adapted to accommodate the beam width of the optics beam 274. In another embodiment, a transmission cable, such as the cable 204 shown in FIG. 2, is coupled to the optics assembly 202 and is disposed through the optical channel 270. In the latter embodiment, the window 272 may be unnecessary and the chamber integrity can be maintained by the provision of seals around the transmission cable.

The receiving assembly 208 includes collection units 217, 219 mounted at the terminal ends of the input transmission cables 214. A first collection unit 217 is disposed with a line-of-sight to the upper surface of the substrate 106. A second collection unit 219 is positioned to have a line-of-sight to the lower surface of the showerhead 116. The collection units 217, 219 include optical structures adapted to collect a portion of the signal reflected from substrate 106 and showerhead 116, respectively. The detector/converter unit 212 is mounted on another end of the input transmission cables 214 to receive and detect the collected signals and transmit the same to the signal processing unit 210.

In operation, an optical beam 274 is directed through the optical channel 270 and onto the substrate 106. The incidence angle of the optical beam 274 is selected to cause the optical beam 274 to be repeatedly reflected between the substrate 106 and the showerhead 116. Accordingly, the optical beam 274 is laterally propagated over a portion of the substrate 106 which may be the full diameter of the substrate 106 or some shorter distance depending on the positioning of the optical channel 270 and the collection units 217, 219. As the optics beam 274 propagates, the topography of the substrate 106 and showerhead 116 will cause the optics beam 274 to be reflected in various directions. Accordingly, the provision of two or more collection units 217, 219 is believed to capture a greater portion of the illumination generated by the optical beam 274. However, in other embodiments, one collection unit may be sufficient.

The collected signals are then transmitted to the detector/converter unit 212 via the input transmission cable 214. As described above, with respect to FIG. 2, the detector/converter unit 212 detects the signal and then provides an output to the signal processing unit 210. The signal processing unit 210 can then provide data pertaining to the reflectivity of the substrate being processed.

Figure 7:
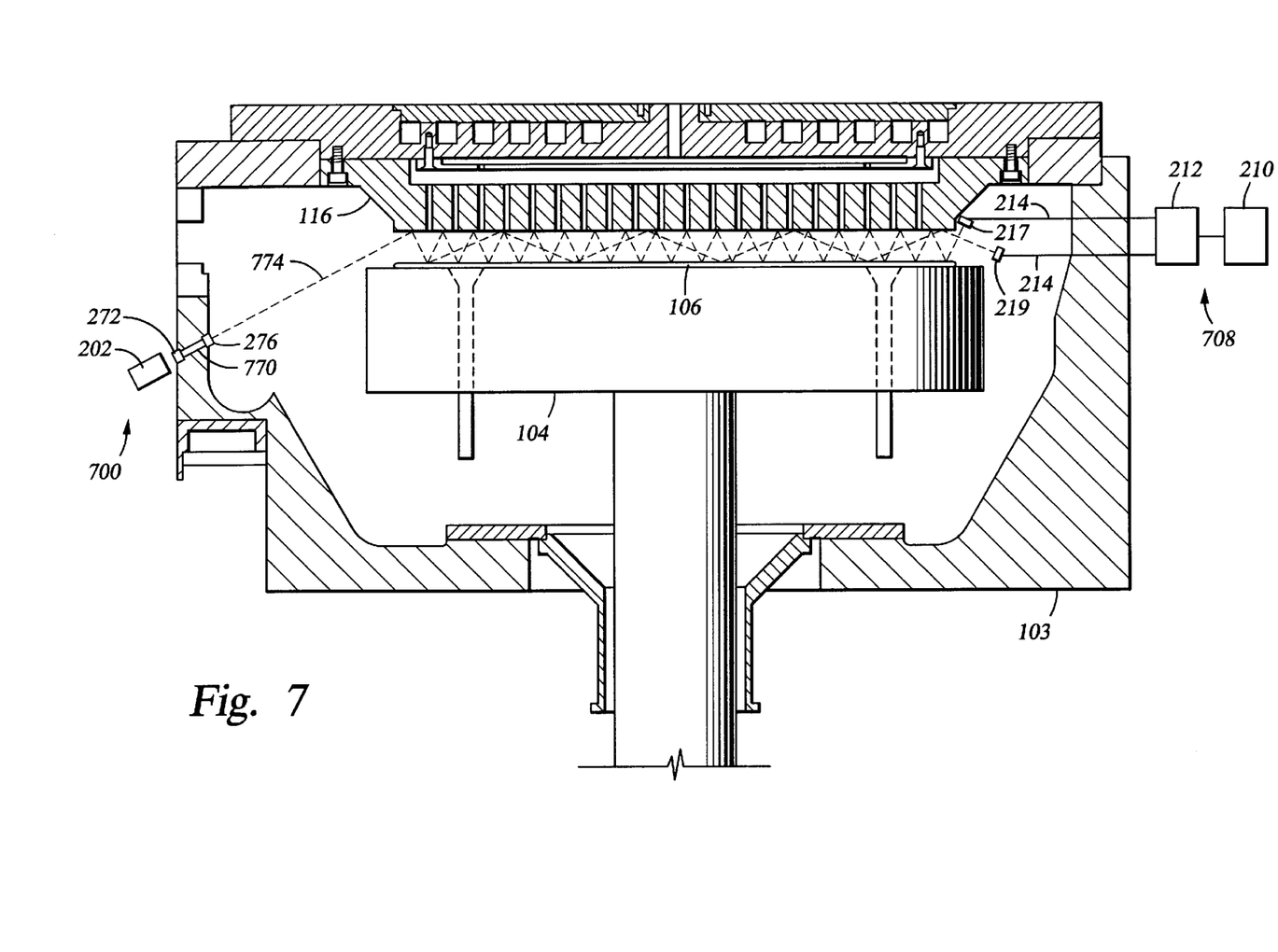
FIG. 7 is another embodiment of a reflectivity monitoring system.

In another embodiment of a reflectivity monitoring system, shown in FIG. 7, an optical channel 770 is formed in the chamber body 103. The optical channel 770 is machined to provide a transmitting assembly 700 a line-of-sight to the showerhead 116. The transmitting assembly 700 and a receiving assembly 708 comprises substantially the same structure and positioning as the assemblies 200 and 208, respectively, described with reference to FIG. 5. Accordingly, an optical beam 774 is directed toward the showerhead 116 at an incident angle selected to cause reflection of the optical beam 774 between the showerhead 116 and the substrate 106. The resulting signals are then collected by the receiving assembly 208 and processed by the signal processing unit 210.

Figure 8:
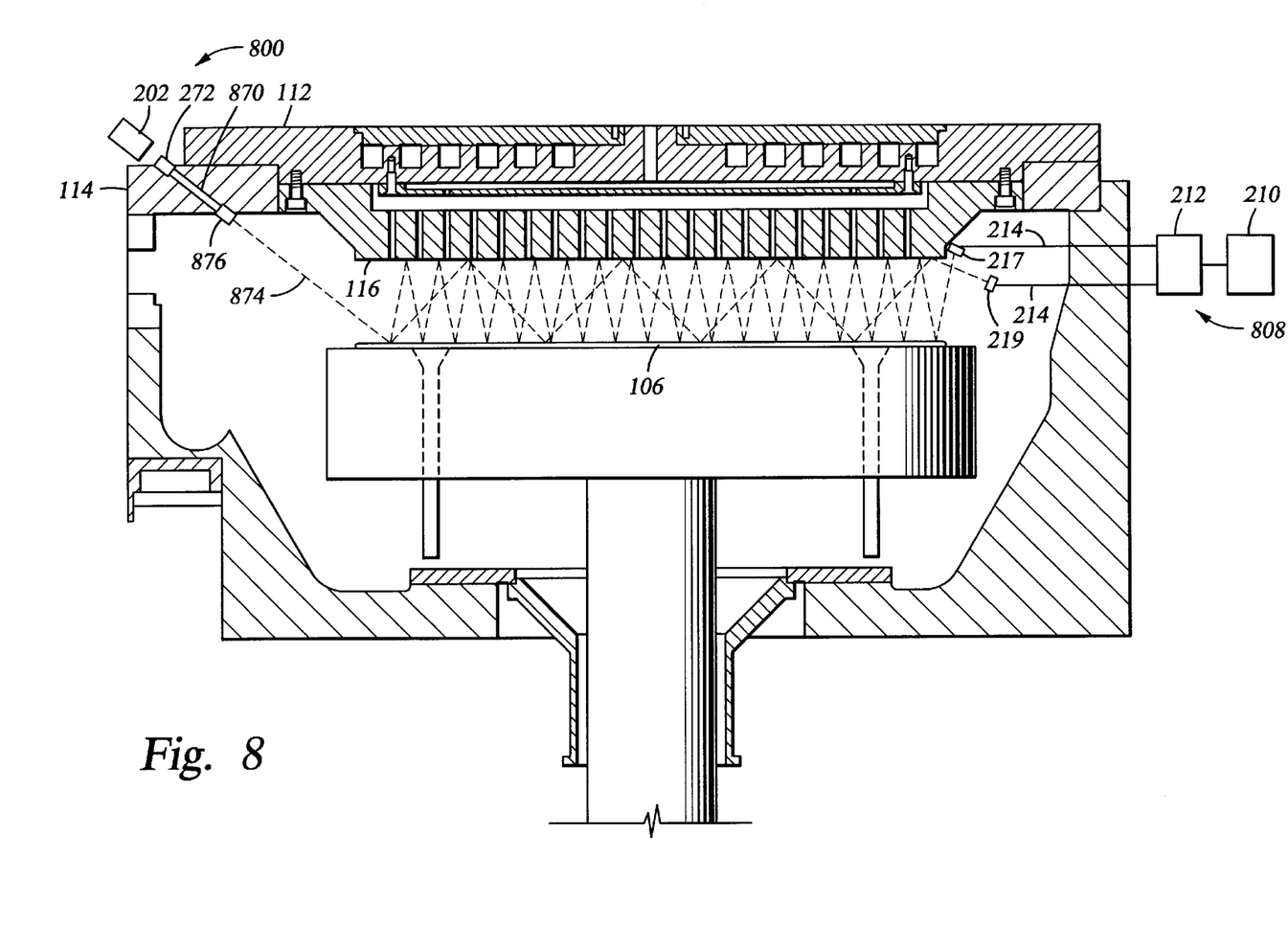
FIG. 8 is another embodiment of a reflectivity monitoring system.

FIGS. 5 and 7 show the pedestal 104 in a raised processing position. Thus, reflectivity measurements can be made during the processing of the substrate 106. However, the reflectivity measurements may be made at any time a substrate is in the field of view (FOV) of the transmitting assembly 200, 700 and the signals reflected from the substrate can be received and detected by the receiving assembly 208, 708. Further, some embodiments of the invention are particularly directed toward measuring the reflectivity of a substrate while in a position other than the raised processing position. For example, FIG. 8 shows an optical channel 870 formed in the lid rim 114 and oriented to provide a transmitting assembly 800 a line-of-sight to an edge of a substrate 106 in a lowered position. Accordingly, an optical beam 874 defined by an optical assembly 876 (e.g., a collimnator) is shown incident at a perimeter portion of the substrate 106. Such an embodiment allows the reflectivity to be measured during delivery of the substrate 106 into the chamber 100 and removal of the substrate 106 from the chamber 100.

The foregoing embodiments are merely illustrative and additional or alternative devices and methods may be employed. Thus, other optical devices may be used to condition the signal provided by the transmitting assembly 200 and/or the signal received by the receiving assembly 208. For example, any known and unknown filtering mechanisms or methods can be used to enhance the signal-to-noise ratio of the reflected signals. The signal qualities may be further refined or conditioned by the use of algorithms executable by the signal processing system 210. Further, it is understood that the embodiments described above may be used together in any combination.

While the foregoing is directed to the preferred embodiment of the present invention, other and further embodiments of the invention may be devised without departing from the basic scope thereof, and the scope thereof is determined by the claims that follow.

What is claimed is:

1. An apparatus for measuring the reflectivity of an object, comprising:
    (a) a vacuum chamber comprising an aperture for transfer of the object therethrough and an opening for transmitting an optical signal from a region external to the vacuum chamber into an internal region of the chamber;
    (b) a transmitting assembly including a light source positioned external to the vacuum chamber and proximate the opening to transmit an optical beam into the internal region;
    (c) a receiving assembly adapted to receive a reflected portion of the optical beam; and
    (d) a signal processing system coupled to the receiving assembly, wherein the signal processing system is programmed to determine the reflectivity of a surface of a substrate disposed in the vacuum chamber.

2. The apparatus of claim 1, wherein the vacuum chamber includes a showerhead and wherein the transmitting assembly includes one or more transmitting cables disposed through the showerhead and adapted to provide the optical beam into the internal region.

3. The apparatus of claim 1, wherein the opening includes an inlet end and an outlet end, wherein a collimator is disposed at the outlet end.

4. The apparatus of claim 1, further comprising a substrate support member disposed in the vacuum chamber and wherein the optical beam is oriented to fall on the substrate support member while in a raised processing position.

5. The apparatus of claim 1, wherein the receiving assembly comprises:
    (e) one or more collection units disposed in the vacuum chamber;
    (f) a signal detector coupled to the one or more collection units; and
    (g) a signal converter coupled to the signal detector and to the signal processing system.

6. The apparatus of claim 5, wherein the signal processing system comprises a signal-bearing medium containing a computer-readable program, which when executed by a processor, causes the signal processing system to generate reflectivity information.

7. An apparatus for measuring the reflectivity of an object, comprising:
    (a) a vacuum chamber body defining an aperture for transfer of the object therethrough;
    (b) a showerhead disposed on the vacuum chamber body;
    (c) a substrate support member disposed in the vacuum chamber body;
    (d) a transmitting assembly comprising:
        (i) a light source positioned in a region external to the vacuum chamber body; and
        (ii) one or more transmitting cables having a light input end disposed proximate the light source and a light output end adapted to deliver an optical beam into an internal region of the vacuum chamber body; wherein at least a portion of the transmitting cable is disposed in the showerhead; and
    (e) a receiving assembly at least a portion of which is disposed in the internal region and is adapted to receive a reflected portion of the optical beam.

8. The apparatus of claim 7, wherein the receiving assembly comprises:
    (f) one or more collection units disposed in the vacuum chamber;
    (g) a signal detector coupled to the one or more collection units; and
    (h) a signal converter coupled to the signal detector and to a signal processing system.

9. The apparatus of claim 7, further comprising a signal processing system coupled to the receiving assembly, wherein the signal processing system is programmed to determine the reflectivity of a surface disposed on the substrate support member.

10. The apparatus of claim 7, wherein the one or more transmitting cables are fiber optics cables.

11. A method of measuring reflectivity of a substrate disposed in a vacuum processing chamber comprising a gas showerhead at one end of the chamber, comprising:
    delivering an optical beam through the showerhead and onto a surface of the substrate; and receiving reflected portions of the optical beam at a signal receiving assembly.

12. The method of claim 11, wherein the step of delivering comprises delivering the optical beam through a fiber optics cable.

13. The method of claim 11, wherein the step of delivering comprises supplying the optical beam from an ultra-violet lamp.

14. The method of claim 11, further comprising processing the reflected portions of the optical beam to determine a reflectivity value of the surface of the substrate.

15. A method of measuring reflectivity of a substrate disposed in a vacuum processing chamber comprising a gas showerhead at one end of the chamber, comprising:

delivering an optical beam from a region lateral of the substrate and onto a surface of the showerhead, wherein the optical beam is reflected from the surface of the showerhead onto the surface of the substrate; and receiving reflected portions of the optical beam at a signal receiving assembly.

16. The method of claim 15, further comprising:

allowing the optical beam to be reflected between the surface of the showerhead and the surface of the showerhead multiple times.

17. The method of claim 15, further comprising processing the reflected portions of the optical beam to determine a reflectivity value of the surface of the substrate.

18. An apparatus for measuring the reflectivity of an object, comprising:

a vacuum chamber comprising an aperture for transfer of the object therethrough and an opening for transmitting an optical signal from a region external to the vacuum chamber into an internal region of the chamber;

a transmitting assembly including a light source positioned external to the vacuum chamber and proximate the opening to transmit an optical beam into the internal region;

a receiving assembly adapted to receive a reflected portion of the optical beam;

a signal processing system coupled to the receiving assembly, wherein the signal processing system is programmed to determine the reflectivity of a surface of a substrate disposed in the vacuum chamber;

a substrate support member disposed in the vacuum chamber; and a showerhead;

wherein the receiving assembly comprises:

a first collection unit oriented and adapted to collect a portion of the optical beam reflected from the substrate support member; and a second collection unit oriented and adapted to collect a portion of the optical beam reflected from the showerhead.

19. The apparatus of claim 18, wherein the transmitting assembly includes one or more transmitting cables disposed through the showerhead and adapted to provide the optical beam into the internal region.

20. The apparatus of claim 18, wherein the opening includes an inlet end and an outlet end, wherein a collimator is disposed at the outlet end.

21. The apparatus of claim 18, wherein the optical beam is oriented to fall on the substrate support member while in a raised processing position.

22. The apparatus of claim 18, wherein the receiving assembly comprises a signal detector coupled to the collection units and a signal converter coupled to the signal detector and to the signal processing system.

23. A method of measuring reflectivity of a substrate disposed in a vacuum processing chamber comprising a gas showerhead at one end of the chamber, comprising:

delivering an optical beam through the showerhead and onto a surface of the substrate; and receiving reflected portions of the optical beam at a signal receiving assembly;

wherein the step of delivering comprises emitting the optical beam onto a surface of the showerhead, wherein the optical beam is reflected from the surface of the showerhead onto the surface of the substrate.

24. The method of claim 23, further comprising allowing the optical beam to be reflected between the surface of the showerhead and the surface of the substrate multiple times before being received by the signal receiving assembly.

25. The method of claim 23, wherein the step of delivering comprises delivering the optical beam through one or more fiber optic cables.

26. The method of claim 23, wherein the step of delivering comprises supplying the optical beam from an ultra-violet lamp.

27. The method of claim 23, further comprising processing the reflected portions of the optical beam to determine a reflectivity value of the surface of the substrate.

* * * * *

UNITED STATES PATENT AND TRADEMARK OFFICE
CERTIFICATE OF CORRECTION

PATENT NO. : 6,381,021 B1  Page 1 of 1
DATED : April 30, 2002
INVENTOR(S) : Somekh et al.

It is certified that error appears in the above-identified patent and that said Letters Patent is hereby corrected as shown below:

Column 5,
Lines 2 and 3, please change "angle O" to -- angle $\theta$ --.

Column 6,
Line 21, please change "generalpurpose" to -- general-purpose --.

Signed and Sealed this

Seventeenth Day of June, 2003

JAMES E. ROGAN
*Director of the United States Patent and Trademark Office*